United States Patent [19]
Bird et al.

[11] Patent Number: 5,859,344
[45] Date of Patent: Jan. 12, 1999

[54] MODIFIED FRUIT CONTAINING GALACTANASE TRANSGENE

[75] Inventors: Colin Roger Bird, Bracknell; Karen Anne Holt, Reading; Sylvie Picard, Taplow; Wolfgang Walter Schuch, Crowthorne; Annette Teresa Carey, Durham; Graham Barron Seymour, Wellesbourne; Gregory Alan Tucker, Shepshed, all of United Kingdom

[73] Assignee: Zeneca Limited, London, United Kingdom

[21] Appl. No.: 687,372

[22] PCT Filed: Oct. 10, 1994

[86] PCT No.: PCT/GB94/02203

§ 371 Date: Aug. 2, 1996

§ 102(e) Date: Aug. 2, 1996

[87] PCT Pub. No.: WO95/10622

PCT Pub. Date: Apr. 20, 1995

[30] Foreign Application Priority Data

Oct. 12, 1993 [GB] United Kingdom ............ 9320930

[51] Int. Cl.⁶ .............. A01H 5/00; C12N 5/14; C12N 15/29; C12N 15/52; C12N 15/82

[52] U.S. Cl. .......... 800/205; 435/172.3; 435/320.1; 435/419; 536/23.2; 536/23.6

[58] Field of Search ............. 47/58; 435/320.1, 435/172.3, 419; 536/23.2, 23.6, 24.2; 800/205, DIG. 9, DIG. 52

[56] References Cited

U.S. PATENT DOCUMENTS 5,296,365 3/1994 Overbeeke et al. ............. 435/208
5,474,922 12/1995 Dorreich et al. ............. 435/200

FOREIGN PATENT DOCUMENTS

| | | |
|---|---|---|
| 0 341 885 | 11/1989 | European Pat. Off. . |
| 0 479 359 | 4/1992 | European Pat. Off. . |
| WOA 87 07641 | 12/1987 | WIPO . |
| WOA 90 10703 | 9/1990 | WIPO . |
| WOA 91 08299 | 6/1991 | WIPO . |
| WOA 92 13945 | 8/1992 | WIPO . |

OTHER PUBLICATIONS

Koziel MG, et al. "Optimizing expression of trangenes with an emphasis on post–transcriptional events." Plant Mol. Biol. 32:393–405, 1996.

Stam M, et al. "The silence of genes in transgenic plants." Ann. Bot. 79: 3–13, 1997.

Smith CJS, et al. "Antisense RNA inhibition of polygalacturonase gene expression in transgenic tomatoes." Nature 334: 724–726, Sep. 25, 1988.

Darnell J, et al. "Molecular Cell Biology." Scientific American Book, NY, pp. 255–257, 1986.

Pressey, R., "Beta–galactosidases in ripening tomatoes", Plant. Physiol., vol. 71, 1983 (pp. 131–135).

Starett, D. A. et al, "Partial purification of alpha–galactosidase, beta–galactosidase, and alpha–mannosidase from ripening tomato fruit", Plant Physiol., vol. 102, No. 1, May 1993.

Raghothama, et al, "Characterization of an ethylene regulated flower senescence–related gene from carnation", Plant Molecular Biology, vol. 17, 1991, pp. 61–71.

*Primary Examiner*—Douglas W. Robinson
*Assistant Examiner*—Amy J. Nelson
*Attorney, Agent, or Firm*—Pillsbury Madison & Sutro LLP

[57] ABSTRACT

The invention provides DNA homologous to a disclosed sequence which encodes a galactosidase/galactanase enzyme. Such DNA is incorporated into DNA constructs which are transformed into plants to increase or decrease expression of the related gene. This provides a method for modifying cell wall metabolism and fruit-ripening characteristics.

9 Claims, No Drawings

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:1:

```
Ser Val Ser Tyr Asp Asp Arg Ala Ile Ile Ile Asn Gly Lys Arg Lys
 1               5                  10                  15
Ile Leu Ile Ser Gly Ser Ile His Tyr Pro Arg Lys Tyr Pro
            20              25                  30
```

( 2 ) INFORMATION FOR SEQ ID NO:2:

( i ) SEQUENCE CHARACTERISTICS:
    ( A ) LENGTH: 2945 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:2:

```
CGGAGGGAGG  AAGTTAGTTC  ATTAGTTCAT  TGCCTTGTAA  AGGCACAATC  TTGATTCTTG     60
ATTTGTTGAC  AAATATGGGT  TTTTGGATGG  CAATGTTGCT  GATGTTGTTA  TTGTGTTTAT    120
GGGTTTCTTG  TGGAATTGCT  TCTGTTTCAT  ATGACCATAA  AGCTATCATT  GTAAATGGAC    180
AAAGAAAAAT  TCTCATTTCT  GGATCCATTC  ACTACCCTAG  AAGCACCCCT  GAGATGTGGC    240
CAGATCTTAT  TCAGAAGGCA  AAAGAAGGGG  GAGTTGATGT  TATACAGACT  TATGTTTTCT    300
GGAATGGGCA  TGAGCCTGAA  GAAGGGAAAT  ATTATTTTGA  AGAGAGGTAT  GATTTAGTGA    360
AGTTCATTAA  AGTGGTGCAA  GAAGCAGGAC  TTTATGTGCA  TCTTAGGATT  GGACCTTATG    420
CATGTGCTGA  ATGGAATTTT  GGGGGTTTTC  CTGTTTGGCT  GAAGTATGTT  CCAGGTATTA    480
GTTTCAGAAC  AAACAATGAG  CCATTCAAGG  CTGCAATGCA  AAAGTTCACT  ACTAAGATTG    540
TTGATATGAT  GAAAGCAGAA  AAGCTCTATG  AAACTCAGGG  TGGTCCAATT  ATTCTATCTC    600
AGATAGAAAA  TGAATATGGA  CCTATGGAGT  GGGAACTAGG  TGAACCTGGT  AAAGTTTACT    660
CAGAATGGGC  AGCCAAAATG  GCTGTGGATC  TTGGCACTGG  TGTCCCATGG  ATCATGTGCA    720
AGCAAGATGA  TGTCCCTGAT  CCTATTATTA  ATACTTGCAA  TGGTTTCTAC  TGTGACTACT    780
TCACACCAAA  TAAGGCTAAT  AAACCAAGA   TGTGGACTGA  AGCCTGGACA  GCCTGGTTTA    840
CCGAATTTGG  AGGTCCAGTT  CCTTACCGTC  CTGCAGAGGA  TATGGCATTT  GCTGTCGCAA    900
GATTTATACA  AACGGGAGGC  TCCTTCATCA  ATTACTATAT  GTATCATGGA  GGAACAAACT    960
TTGGAAGGAC  TTCTGGTGGC  CCATTTATTG  CTACTAGTTA  TGATTATGAT  GCACCCCTAG   1020
ATGAATTTGG  GTCATTACGG  CAGCCTAAAT  GGGGTCATCT  GAAAGATCTA  CATAGAGCAA   1080
```

| | | | | | | |
|---|---|---|---|---|---|---|
| TAAAGCTCTG | TGAGCCAGCT | TTAGTATCTG | TAGATCCAAC | TGTGACATCC | TTAGGAAACT | 1140 |
| ATCAAGAGGC | ACGTGTTTTC | AAGTCAGAGT | CTGGGGCCTG | CGCTGCCTTC | CTAGCAAATT | 1200 |
| ACAACCAGCA | CTCTTTTGCT | AAAGTGGCAT | TTGGGAACAT | GCATTATAAC | TTGCCACCCT | 1260 |
| GGTCTATCAG | CATTCTTCCC | GACTGCAAGA | ACACTGTCTA | TAATACTGCA | AGGGTTGGTG | 1320 |
| CTCAAAGTGC | TCAGATGAAG | ATGACTCCAG | TCAGTAGAGG | ATTCTCATGG | GAGTCATTCA | 1380 |
| ATGAAGACGC | AGCATCGCAT | GAAGACGACA | CTTTCACAGT | TGTTGGGTTA | TTGGAGCAGA | 1440 |
| TTAATATCAC | AAGAGATGTA | TCTGATTACT | TGTGGTATAT | GACTGACATT | GAGATTGATC | 1500 |
| CAACAGAAGG | ATTTTTGAAT | AGTGGAAATT | GGCCTTGGCT | TACTGTCTTC | TCTGCTGGCC | 1560 |
| ATGCATTGCA | TGTATTCGTG | AATGGTCAAT | TAGCAGGAAC | TGTGTACGGA | AGTTTAGAAA | 1620 |
| ACCCAAAACT | AACTTTCAGC | AACGGTATAA | ATCTGAGAGC | TGGTGTGAAC | AAGATTTCTC | 1680 |
| TGCTAAGCAT | TGCTGTTGGT | CTTCCGAACG | TTGGCCCTCA | TTTTGAGACA | TGGAATGCTG | 1740 |
| GTGTTCTTGG | ACCAGTTTCA | CTTAATGGAC | TTAATGAAGG | AACAAGAGAT | TAACATGGC | 1800 |
| AGAAATGGTT | CTACAAGGTT | GGTCTAAAAG | GAGAAGCCCT | GAGTCTTCAT | TCACTCAGTG | 1860 |
| GTAGCCCATC | CGTGGAGTGG | GTGGAAGGCT | CTTTAGTGGC | TCAGAAGCAG | CCACTCAGTT | 1920 |
| GGTATAAGAC | TACATTCAAT | GCTCCAGATG | GAAATGAACC | TTTGGCTTTA | GATATGAATA | 1980 |
| CCATGGGCAA | AGGTCAAGTA | TGGATAAATG | GTCAGAGCCT | CGGACGCCAC | TGGCCTGCAT | 2040 |
| ATAAATCATC | TGGAAGTTGT | AGTGTCTGTA | ACTATACTGG | CTGGTTTGAT | GAGAAAAAGT | 2100 |
| GCCTAACTAA | CTGTGGTGAG | GGCTCACAAA | GATGGTACCA | CGTACCCCGG | TCTTGGCTGT | 2160 |
| ATCCTACTGG | AAATTTGTTA | GTTGTATTCG | AGGAATGGGG | AGGAGATCCT | TATGGAATCA | 2220 |
| CTTTAGTCAA | AAGAGAAATA | GGGAGTGTTT | GTGCTGATAT | ATATGAGTGG | CAACCACAGT | 2280 |
| TATTGAATTG | GCAGAGGCTA | GTATCTGGTA | AGTTTGACAG | ACCTCTCAGA | CCTAAAGCCC | 2340 |
| ATCTTAAGTG | TGCACCTGGT | CAGAAGATTT | CTTCAATCAA | ATTTGCAAGC | TTTGGAACAC | 2400 |
| CAGAGGGAGT | TTGTGGGAAC | TTCCAGCAGG | GAAGCTGCCA | TGCTCCGCGC | TCATATGATG | 2460 |
| CTTTCAAAAA | GAATTGTGTT | GGGAAAGAGT | CTTGCTCAGT | ACAGGTAACA | CCAGAGAATT | 2520 |
| TTGGAGGTGA | TCCATGTCGA | AACGTTCTAA | AGAAACTCTC | AGTGGAAGCC | ATTTGTAGTT | 2580 |
| GATGATTCTG | AGTATACAAG | TGAAAAAATA | CTTGAACCAC | TCATATAAAC | ATTTTTCAAA | 2640 |
| CGAGCTACTA | GACATCCATT | AACCCACACT | ACCATTTTTT | GGCTTTGCTG | GGGTTGAAGT | 2700 |
| TGTACAGTTA | AGCAACACAC | CTCTTTGATC | AAAGCTCACC | TGATTATGAA | GATGATTGAC | 2760 |
| GAAAGATTCT | GTACATGTAA | GGTTTCGTCT | AATTACACAT | ACAGATATGA | TTCTTGATGA | 2820 |
| ATCGATGTGC | AAATTTTGTT | TGTGTTAGGG | TGAGAGAGAC | TTGAAAAGCA | TTTTGCTTTC | 2880 |
| ATGATGTTCT | ACATTATACA | ATCATAATGT | AAGTAAGCAA | GCAATAATTC | ATTGCTTTGC | 2940 |
| ACCCG | | | | | | 2945 |

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

AAYGGNAARM GNAARATNYT NAT          23

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

ATNYACTACC MNCGNRAATA    20

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

ATNCAYTAYC CNMGNAARTA YCC    23

(2) INFORMATION FOR SEQ ID NO:6:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Asn Val Trp Tyr Asp Tyr Arg Ala Ile Lys Ile Asn Asp Gln Arg Arg
 1              5                   10                  15

Ile Leu Leu Ser Gly Ser Ile His Tyr Pro Arg Ser Thr Pro
              20                 25               30

(2) INFORMATION FOR SEQ ID NO:7:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Ser Val Ser Tyr Asp His Lys Ala Ile Ile Val Asn Gly Gln Arg Lys
 1              5                   10                  15

Ile Leu Ile Ser Gly Ser Ile His Tyr Pro Arg Ser Thr Pro
              20                 25               30

MODIFIED FRUIT CONTAINING GALACTANASE TRANSGENE

BACKGROUND OF THE INVENTION

1. Field of the Invention

This invention relates to the modification of plant gene expression causing modification of cell wall metabolism in plants.

2. Description of the Related Art

The modification of plant gene expression has been achieved by several methods. The molecular biologist can choose from a range of known methods to decrease or increase gene expression or to alter the spatial or temporal expression of a particular gene. For example, the expression of either specific antisense RNA or partial (truncated) sense RNA has been utilised to reduce the expression of various target genes in plants (as reviewed by Bird and Ray, 1991, Biotechnology and Genetic Engineering Reviews 9:207–227). These techniques involve the incorporation into the genome of the plant of a synthetic gene designed to express either antisense or sense RNA. They have been successfully used to down-regulate the expression of a range of individual genes involved in the development and ripening of tomato fruit (Gray et al, 1992, Plant Molecular Biology, 19:69–87). Methods to increase the expression of a target gene have also been developed. For example, additional genes designed to express RNA containing the complete coding region of the target gene may be incorporated into the genome of the plant to "over-express" the gene product. Various other methods to modify gene expression are known; for example, the use of alternative regulatory sequences.

The primary cell walls of fruit are important constituents that influence the physical and eating properties of fresh fruit and processed products. During fruit development and ripening, many biochemical changes occur that determine the composition, texture and quality of the ripe fruit. Fruit cell walls are continually modified by both synthetic and degradative processes as the fruit expand and eventually ripen. There are three major classes of polysaccharide in the cell wall: pectins, hemicelluloses and celluloses. These polysaccharide fractions undergo significant modifications in structure during ripening. Some of the most apparent of these occur in the pectic fraction including polyurinide solubilization, depolymerisation and a loss of wall arabinosyl and galactosyl residues (Gross and Wallner, 1979, Plant Physiol, 63:117–120; Gross, 1984, Physiol Plant, 62:25–32; Seymour et al, 1987, Phytochem, 26:1871–1875). Several pectin degrading enzymes have been isolated from tomato, including polygalacturonase and pectinesterase. Another important group of pectolytic enzymes are those which degrade the neutral sugar component, where galactosyl and arabinosyl residues occur as sidechains attached to a rhamnosyul unit in the main galacturonan backbone. Specific information on the structure of these sidechains is sparse due to their complexity, but in many plant tissues, including those from tomato fruit (Seymour et al, 1990, Phytochemistry, 29:725–731), chains of (1->4)-β-D-galactan and (1->5) -linked arabinofuranosyl units are common (Carpita and Gibeaut, 1993, Plant J, 3:1–30). Fleshy fruits, including tomato, show a loss of wall galactosyl residues during ripening (Bartley, 1976, Phytochem, 15:625–626; Gross,1984, Physiol Plant, 62:25–32; Gross and Sams, 1984, Phytochemistry, 23:2457–2461; Redgwell et al, 1992, Plant Physiol, 98:71–81) and in tomato and kiwifruit, these changes are accompanied by an accumulation of free galactose (Gross, 1983, Phytochem, 22:1137–1139; Ogawa et al, 1990, J Jap Soc Food Sci, 37:298–305). The increased loss of cell wall galactosyl residues during ripening appears to be the result of increased solubilisation of galactosyl residues from the cell wall (Kim et al, 1991, Postharvest Biology and Technology, 1:67–80; Seymour et al, 1990, Phytochemistry, 29:725–731). The loss of cell wall galactose has also been reported in non-fruit tissues such as senescencing carnation petals (de Vetten and Huber, 1990, Physiol Plant, 78:447–454). Evidence indicates that these events are likely to result from the action of a β-galactosidase/galactanase which acts on galactan-rich pectins.

β-galactosidase activity has been detected in fruits including apple (Bartley, 1976, Phytochem, 15:625–626; Dick et al, 1990, Physiol Plant, 80:250–256), avocado (De Veau et al, 1993, Physiol Plant, 87:279–285), kiwifruit (Ogawa et al, 1990, J Jap Soc Food Sci Tech, 37:298–305; Ross et al, 1993, Planta, 189:499–506), muskmelon (Ranwala et al, 1992, Plant Physiology, 100:1318–1325) and tomato (Pressey, 1983, Plant Physiology, 71:132–135). In several fruit, including apple (Bartley IM, 1990, Phytochemistry, 13:2107–2111) and pepper (Gross et al, Physiol Plant, 66:31–36) there are large increases in galactosidase activity during ripening. However, in most cases the natural substrates for the galactosidase activity have not been identified.

In tomato three different β-galactosidase activities were detected and partially purified, but only one of the isoforms (β-galactosidase II, which increased in activity during ripening) could degrade a (1->4)-β-D-galactan isolated from tomato cell walls (Pressey, 1983, Plant Physiology, 71:132–135; Pressey and Himmelsbach, 1984, Carbohydr Res, 127:356–359). The enzyme was therefore identified as an exo-(1->4)-β-D-galactanase. Detailed studies on the composition and structure of tomato cell wall polysaccharhides by Seymour et al (1990, Phytochemistry, 29:725–731) demonstrated that galactans with this linkage predominate in tomato and undergo degradation during ripening. The free galactose measured in ripening tomato fruit is likely to result from this hydrolytic activity rather than altered metabolic utilization (Kim et al, 1991, Postharvest Biology and Technology, 1:67–80). The role of galactanase in tomato fruit ripening remains unknown, but it may play a key part in fruit softening. Galactan degrading enzymes have also been isolated from ripening avocado (De Veau et al, 1993, Physiol Plant, 87:279–285) and kiwifruit (Ross et al, 1993, Planta, 189:499–506).

Pectic polysaccharides in fruit consist mainly of an α-1, 4-galactosyluronic acid backbone with 2- and 2,4-linked rhamnosyl residues interspersed in the chain (McNeil et al, 1984, Ann Rev Biochem, 53:625–663). The 2,4-linked rhamnosyl residues are thought to act as attachment points for sidechains of β1,4-galactosyl and α1,5-linked arabinosyl residues (Seymour et al, 1990, Phytochemistry, 29:725–731). The role of the galactan rich side chains in the cell wall has not been confirmed. However, it is likey that they increase the interactions between cell wall components. Several mechanisms for these interactions are possible, for example: covalent links between galacturonan polymers; non-covalent interaction of pectin side chains; interactions with other cell wall components. The loss of galactosyl side chains from the pectin coincides with the major changes in texture that occur during fruit ripening.

SUMMARY OF THE INVENTION

According to a first aspect of the present invention, there is provided a method to modify cell wall metabolism comprising modification of the activity of at least one galactosidase. In particular, the method may be used to modify fruit ripening characteristics.

The levels of galactosidase may be either reduced or increased during development and ripening depending on the ripening characteristics desired for the modified fruit. "Antisense" or "partial sense" or other techniques may be used to reduce the expression of galactosidase in developing and ripening fruit. The levels of galactosidase may also be increased; for example, by incorporation of additional galactosidase genes. The additional genes may be designed to give either the same or different spatial and temporal patterns of expression in the fruit.

Reduced activity of galactosidase can be used to modify various aspects of fruit quality, including:

a. Increased fruit firmness;
b. Improved resistance to mechanical damage during harvest and subsequent handling;
c. Improved texture of ripe fruit;
d. Improved resistance to fruit diseases;
e. Improved viscosity of processed fruit;

Increased activity of galactosidase can be used to modify various aspects of fruit quality, including:

a. Modified fruit texture;
b. Modified processing properties.

In work leading to this invention, we have isolated a protein from tomato that has galactosidase activity. The protein has been shown to act as a galactanase by its ability to release free galactose from a polymeric carbohydrate that contains predominantly β1-4 linked galactan. This tomato galactanase enzyme was purified to a single polypeptide and N-terminal sequence analysis yielded the sequence shown as SEQ ID NO 1. This sequence shows homology to an amino acid sequence encoded by a β-galactosidase gene from *Aspergillus niger* (International Patent Application of Hartley et al, PCT/GB90/00373) and also by an un-identified senescence related clone from carnation (Raghothama et al, 1991, Plant Molecular Biology, 17:61–71). Degenerate oligonucleotides from this amino acid sequence were used to identify and isolate DNA encoding the galactanase enzyme.

According to a second aspect of the present invention there is provided a DNA sequence encoding a plant galactanase. The galactanase is an isoform of a galactosidase which degrades galactans. The DNA sequence may be derived from cDNA, from genomic DNA or may be synthesised ab initio.

A cDNA clone encoding a galactanase has been obtained from a tomato cDNA library. The clone is hereinafter called KH15. The nucleotide sequence of the galactanase cDNA (clone KH15) is given as SEQ ID NO 2. The clone KH15 (in lambda phage) was deposited at The National Collections of Industrial and Marine Bacteria (23 St Machar Drive, Aberdeen, Scotland, AB2 1RY) under the terms of the Budapest Treaty on 11 May 1994 under the accession number NCIMB 40639.

An alternative source of the DNA sequence is a suitable gene encoding a galactanase. This gene may differ from the corresponding cDNA in that introns may be present. The introns are not transcribed into mRNA (or, if so transcribed, are subsequently cut out). Oligonucleotide probes or the cDNA clone may be used to isolate the actual galactanase gene(s) by screening genomic DNA libraries. Such genomic clones may include control sequences operating in the plant genome. Thus it is also possible to isolate promoter sequences which may be used to drive expression of the enzymes or any other protein. These promoters may be particularly responsive to certain developmental events (such as ripening) and environmental conditions. Galactanase gene promoters may be used to drive expression of any target gene.

A galactanase DNA sequence may be isolated from cDNA or genomic DNA libraries of any suitable plant species using oligonucleotide probes based on the KH15 sequence. Bacterial, fungal and algal DNA libraries may also be probed for galactanase sequences. A galactanase DNA sequence is any sequence which cross-hybridises with SEQ ID NO 2, preferably having at least 60% homology with SEQ ID NO 2. A galactanase DNA sequence may encode a protein which is homologous to the predicted gene product encoded by SEQ ID NO 2.

A further way of obtaining a galactanase DNA sequence is to synthesise it ab initio from the appropriate bases, for example using the appropriate cDNA sequence as a guide.

Some or all of the galactanase sequence may be incorporated into DNA constructs suitable for plant transformation. These DNA constructs may then be used to modify galactanase gene expression in plants. "Antisense" or "partial sense" or other techniques may be used to reduce galactanase gene expression in plant tissue (down-regulation). The levels of expression may also be increased (up-regulation); for example, by incorporation of additional galactanase genes. The additional genes may be designed to give either the same or different spatial and temporal patterns of expression in the plant.

According to a further aspect of the invention there is provided a DNA construct comprising some or all of a galactanase DNA sequence under the control of a transcriptional initiation region operative in plants, so that the construct can generate RNA in plant cells.

The cell wall characteristics and related characteristics of plant parts may be modified by transformation with a DNA construct according to the invention. The invention also provides plant cells containing such constructs; plants derived therefrom having modified galactanase gene expression; and seeds of such plants.

A DNA construct according to the invention may be an "antisense" construct generating "antisense" RNA or a "sense" construct (encoding at least part of the functional enzyme) generating "sense" RNA. "Antisense RNA" is an RNA sequence which is complementary to a sequence of bases in the corresponding mRNA: complementary in the sense that each base (or the majority of bases) in the antisense sequence (read in the 3' to 5' sense) is capable of pairing with the corresponding base (G with C, A with U) in the mRNA sequence read in the 5' to 3' sense. Such antisense RNA may be produced in the cell by transformation with an appropriate DNA construct arranged to generate a transcript with at least part of its sequence complementary to at least part of the coding strand of the relevant gene (or of a DNA sequence showing substantial homology therewith). "Sense RNA" is an RNA sequence which is substantially homologous to at least part of the corresponding mRNA sequence. Such sense RNA may be produced in the cell by transformation with an appropriate DNA construct arranged in the normal orientation so as to generate a transcript with a sequence identical to at least part of the coding strand of the relevant gene (or of a DNA sequence showing substantial homology therewith). Suitable sense constructs may be used to inhibit gene expression (as described in International Patent Publication W091/08299) or a sense construct encoding and expressing the functional enzyme may be transformed into the plant to over-express the enzyme.

DNA constructs according to the invention may comprise a base sequence at least 10 bases (preferably at least 35 bases) in length for transcription into RNA. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

As a source of the DNA base sequence for transcription, a suitable cDNA or genomic DNA or synthetic polynucleotide may be used. The isolation of suitable galactanase sequences is described above. Sequences coding for the whole, or substantially the whole, of the enzyme may thus be obtained. Suitable lengths of this DNA sequence may be cut out for use by means of restriction enzymes. When using genomic DNA as the source of a partial base sequence for transcription it is possible to use either intron or exon regions or a combination of both.

To obtain constructs suitable for modifying expression of galactanase in plant cells, the cDNA sequence as found in the enzyme cDNA or the gene sequence as found in the chromosome of the plant may be used. Recombinant DNA constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence is then cloned into a vector containing upstream promoter and downstream terminator sequences. If antisense DNA is required, the cloning is carried out so that the cut DNA sequence is inverted with respect to its orientation in the strand from which it was cut.

In a construct expressing antisense RNA, the strand that was formerly the template strand becomes the coding strand, and vice versa. The construct will thus encode RNA in a base sequence which is complementary to part or all of the sequence of the enzyme mRNA. Thus the two RNA strands are complementary not only in their base sequence but also in their orientations (5' to 3').

In a construct expressing sense RNA, the template and coding strands retain the assignments and orientations of the original plant gene. Constructs expressing sense RNA encode RNA with a base sequence which is homologous to part or all of the sequence of the mRNA. In constructs which express the functional enzyme, the whole of the coding region of the gene is linked to transcriptional control sequences capable of expression in plants.

For example, constructs according to the present invention may be made as follows. A suitable vector containing the desired base sequence for transcription (such as the KH15 cDNA clone) is treated with restriction enzymes to cut the sequence out. The DNA strand so obtained is cloned (if desired, in reverse orientation) into a second vector containing the desired promoter sequence and the desired terminator sequence. Suitable promoters include the 35S cauliflower mosaic virus promoter and the tomato polygalacturonase gene promoter sequence (Bird et al, 1988, Plant Molecular Biology, 11:651–662) or other developmentally regulated fruit promoters. Suitable terminator sequences include that of the *Agrobacterium tumefaciens* nopaline synthase gene (the nos 3' end).

In a DNA construct according to the invention, the transcriptional initiation region may be derived from any plant-operative promoter. The transcriptional initiation region may be positioned for transcription of a DNA sequence encoding RNA which is complementary to a substantial run of bases in a mRNA encoding the galactanase enzyme (making the DNA construct a full or partial antisense construct).

The transcriptional initiation region (or promoter) operative in plants may be a constitutive promoter (such as the 35S cauliflower mosaic virus promoter) or an inducible or developmentally regulated promoter (such as fruit-specific promoters), as circumstances require. For example, it may be desirable to modify galactanase activity only during fruit development and/or ripening. Use of a constitutive promoter will tend to affect enzyme levels and functions in all parts of the plant, while use of a tissue specific promoter allows more selective control of gene expression and affected functions (eg fruit colouration). Thus in applying the invention it may be found convenient to use a promoter that will give expression during fruit development and/or ripening. Thus the antisense or sense RNA is only produced in the organ in which its action is required. Fruit development and/or ripening-specific promoters that could be used include the ripening-enhanced polygalacturonase promoter (International Patent Publication Number WO92/08798), the EB promoter (Diekman & Fischer, 1988, EMBO, 7:3315–3320) and the fruit specific 2A11 promoter (Pear et al, 1989, Plant Molecular Biology, 13:639–651).

The DNA constructs of the invention may be inserted into plants to regulate the expression of galactanase genes and the production of galactanase enzymes, resulting in modification of plant characteristics (in particular fruit-ripening). Depending on the nature of the construct, the production of the galactanase may be increased, or reduced, either throughout or at particular stages in the life of the plant. Generally, as would be expected, production of the enzyme is enhanced only by constructs which express RNA homologous to the substantially complete endogenous enzyme mRNAs. Full-length sense constructs may also inhibit enzyme expression. Constructs containing an incomplete DNA sequence shorter than that corresponding to the complete gene generally inhibit the expression of the gene and production of the enzymes, whether they are arranged to express sense or antisense RNA. Full-length antisense constructs also inhibit gene expression.

A DNA construct of the invention is transformed into a target plant cell. The target plant cell may be part of a whole plant or may be an isolated cell or part of a tissue which may be regenerated into a whole plant. The target plant cell may be selected from any monocotyledonous or dicotyledonous plant species. Plants may be derived from the transformed plant cell by regeneration of transformants and by production of successive generations of the transformants' progeny.

Constructs according to the invention may be used to transform any plant using any suitable transformation technique to make plants according to the invention. Both monocotyledonous and dicotyledonous plant cells may be transformed in various ways known to the art. In many cases such plant cells (particularly when they are cells of dicotyledonous plants) may be cultured to regenerate whole plants which subsequently reproduce to give successive generations of genetically modified plants. Any suitable method of plant transformation may be used. For example, dicotyledonous plants such as tomato and melon may be transformed by Agrobacterium Ti plasmid technology, such as described by Bevan (1984, Nucleic Acid Research, 12:8711–8721) or Fillatti et al (Biotechnology, July 1987, 5:726–730). Such transformed plants may be reproduced sexually, or by cell or tissue culture.

Examples of genetically modified plants according to the present invention include all fruit-bearing plants (such as tomatoes, mangoes, peaches, apples, pears, strawberries, bananas, melons, peppers, chillies, paprika). Other plants that may be modified by the process of the invention include tubers such as radishes, turnips and potatoes, as well as cereals such as maize (corn), wheat, barley and rice.

Use of the galactanase constructs allows modification of galactanase enzyme activity and thus provides a method for modification of plant characteristics, particularly cell walls and fruit-ripening. The overall level of galactanase activity and the relative activities of other enzymes affect plant development and thus determine certain characteristics of the plant parts. Modification of galactanse activity can therefore be used to modify various aspects of plant (including fruit) quality. The activity levels of the enzyme may be either increased or reduced during development depending on the characteristics desired for the modified plant. The galactanase gene may also be expressed in cells, tissues and organisms that do not normally produce the enzyme.

Galactanase gene expression (and hence plant characteristics) may be modified to a greater or lesser extent by controlling the degree of the sense or antisense mRNA production in the plant cells. This may be done by suitable choice of promoter sequences, or by selecting the number of copies or the site of integration of the DNA sequences that are introduced into the plant genome. For example, the DNA construct may include more than one galactanase DNA sequence or more than one recombinant construct may be transformed into each plant cell.

It is also possible to modify galactanase activity while also modifying the activity of one or more other enzymes. For example, the other enzymes may be involved in cell metabolism or in fruit development and ripening. Cell wall metabolising enzymes that may be modified in combination with galactanase include but are not limited to: pectin esterase, polygalacturonase, β-glucanase. Other enzymes involved in fruit development and ripening that may be modified in combination with galactanase include but are not limited to: ethylene biosynthetic enzymes, carotenoid biosynthetic enzymes, carbohydrate metabolism enzymes including invertase.

Several methods are available for modification of galactanase activity in combination with other enzymes. For example, a first plant may be individually transformed with a galactanase construct and then crossed with a second plant which has been individually transformed with a construct encoding another enzyme. As a further example, plants may be either consecutively or co-transformed with galactanase constructs and with appropriate constructs for modification of the activity of the other enzyme(s). An alternative example is plant transformation with a galactanase construct which itself contains an additional gene for modification of the activity of the other enzyme(s). The galactanase constructs may contain sequences of DNA for regulation of the expression of the other enzyme(s) located adjacent to the galactanase sequences. These additional sequences may be in either sense or antisense orientation as described in International patent application publication number WO93/23551 (single construct having distinct DNA regions homologous to different target genes). By using such methods, the benefits of modifying the galactanase activity may be combined with the benefits of modifying the activity of other enzymes.

According to a third aspect of the invention, there is provided a method for modifying galactanase gene expression in plants by transforming plants with galactanase DNA constructs and growing such transformed plants or their descendants followed by selection of plants having modified galactanase gene expression. Suitable galactanase DNA constructs may be adapted to enhance the production of the galactanase enzyme or to inhibit such production by the plant when compared with untransformed plants.

This method may be used for modifying fruit-ripening characteristics: fruit-bearing plants are transformed with galactanase DNA constructs, the transformed plants or their descendants are grown and plants having modified fruit-ripening characteristics are selected.

In this way, plants can be generated which have modified fruit-ripening characteristics due to promotion or inhibition of galactanase gene expression. Similar modifications may be possible using traditional plant breeding techniques, but the present invention provides a means of transferring the trait into elite lines without a prolonged breeding programme which might alter other traits at the same time. As already discussed, plants produced by the method of the invention may also contain other recombinant constructs, for example constructs having other effects on fruit ripening (such as constructs inhibiting the production of polygalacturonase or pectinesterase, or interfering with ethylene production). Fruit containing both types of recombinant construct may be made either by successive transformations, or by crossing two varieties that each contain one of the constructs and selecting among the progeny for those that contain both.

DESCRIPTION OF PREFERRED EMBODIMENTS

The invention will now be described by way of example only, with reference to the sequence listing in which:

SEQ ID NO 1 shows the N-terminal amino acid sequence of tomato galactanase;

SEQ ID NO 2 shows the nucleotide sequence of tomato galactanase (KH15 cDNA);

SEQ ID NO 3 shows the nucleotide sequence of probe KAH3;

SEQ ID NO 4 shows the nucleotide sequence of probe KAH10;

SEQ ID NO 5 shows the nucleotide sequence of probe KAH11;

SEQ ID NO 6 shows the N-terminal amino acid sequence of the protein encoded by clone pSR12;

SEQ ID NO 7 shows the N-terminal amino acid sequence of the protein encoded by clone KH15.

EXAMPLE 1

Partial purification of (1-4)-β-galactanase from tomato fruit

Pericarp tissue (1 kg) from fresh, red-ripe tomatoes (cv. Better Boy) was homogenized with 1.4 l of cold water. All of the subsequent steps were conducted at 4° C. or less. The suspension was stirred for 30 min and solid NaCl added to a final concentration of 1.0M. The pH was adjusted to 6 with 2M NaOH and stirred for 1 hr. The suspension was then centrifuged at 8000 g for 20 min, and ammonium sulphate added to the supernatant solution to 80% of saturation. The precipitated proteins were collected by centrifugation at 20,000 g for 30 min, suspended in 50 ml water and dialysed against 0.15M NaCl for 2 days with one change of buffer. This solution was then centrifuged at 8000 g for 10 min to remove precipitated material. The supernatant represented the crude extract.

The crude extract was loaded onto DEAE-Sephadex A-50 (4.4×90 cm) which had been pre-equilibrated with 50 mM sodium acetate pH 6.0 containing 0.1M NaCl. The sample was eluted with the same buffer and 9.8 ml fractions were collected. Fractions were assayed for β-galactosidase activity (FIG. 1) identifying two peaks of activity—Peak A (Fractions 37–48) and Peak B (Fractions 54–72). Peak A was pooled and concentrated by ultrafiltration using an Amicon Corp. model 52 unit and PM-10 membranes. The concentrated enzyme solution was then chromatographed on a gel permeation column (Sephadex G-100, 2.1×85 cm), with a column buffer of 0.15M NaCl. Peak A was resolved into two peaks of β-galactosidase activity (FIG. 2), designated β-galactosidase I (Fractions 20–23; approximate MW 150,000) and β-galactosidase II (Fractions 26–33; approximate MW 60,000). β-galactosidase II was further purified by chromatography on CM-Cellulose (2.6×18 cm) which had been pre-equilibrated with 50 mM sodium acetate pH5.2. The column was eluted with a linear 0–0.5M NaCl gradient in the same buffer. One peak of β-galactosidase activity was identified (FIG. 3). Active fractions (62–65) were pooled, dialysed against water and concentrated. This fraction was regarded as the purified enzyme. SDS-PAGE of pooled fractions identified a 75 kD protein that was the major protein in the active fractions and was almost absent in the adjacent fractions. This was tentitatively identified as the β-galactosidase protein.

EXAMPLE 2

Assay of β-galactosidase and (1-4)-β-galactanase activity

β-galactosidase activity was assayed by measuring the rate at which p-nitrophenyl-β-galactopyranoside (Sigma) was hydrolysed. The reaction mixture consisted of 0.5 ml of 0.1M citrate (pH4.0), 0.4 ml of 0.1% BSA, 0.1 ml of diluted enzyme and 0.4 ml of 13 mM substrate. After 15 min incubation at 37° C., the reaction was terminated by the addition of 2.0 ml of 0.2M sodium carbonate, and the liberated p-nitrophenol was measured at 415 nm (Pressey, 1983, Plant Physiology, 71:132–135).

Galactanase activity was assayed by measuring the release of reducing sugars and specifically monomeric galactose from a galactose-rich polysaccharide isolated from spruce (60% galactose, 30% mannose and 10% glucose) and also cell wall material isolated from unripe tomato (cv. Ailsa Craig) fruits by the PAW extraction method (Seymour et al 1990 Phytochemistry 29:725–731). $^{13}$C NMR analysis of the spruce galactan identified β-1,4 linkages between galactose units. The reaction mixture consisted of 0.2 ml of 0.1M sodium acetate buffer pH4.0, 0.2 ml of enzyme solution diluted with 0.2k BSA and 0.1 ml Of 1% spruce galactan. The equivalent of 0.05 μmol/min of β-galactosidase activity was used in each assay. Assays were incubated at 37° C. for 4 hr.

Reducing sugars were determined according to Nelson (1944 Journal of Biological Chemistry 153:375–380). Galactose was assayed by terminating the reaction by boiling for 20 min. Samples were cooled in an ice bath and centrifuged at 10,000 g for 5 min to remove precipitated material. The supernatant was stored at −20° C. prior to the determination of D(+) galactose using the Boehringer-Mannheim Lactose/D-Galactose enzymatic test kit.

The purified β-galactosidase II (from Example 1) demonstrated galactanase activity as shown by the release of galactose from both spruce galactan and the tomato fruit cell wall extract:

| Substrate | Reducing sugar released (nmol/2mg substrate) | Galactose released (μg/2mg substrate) |
|---|---|---|
| Spruce galactan | 178 | 37.8 |
| Tomato cell wall | 72 | 13.1 |

The other peaks of β-galactosidase activity from the three column chromatography steps (example 1) did not release galactose from either substrate.

EXAMPLE 3

Isolation of β-galactanase peptide and N-terminal sequence analysis

15 μg of partially purified β-galactosidase (example 1) was run on SDS-PAGE (10% acrylamide) and then blotted onto PVDF ProBlott (Applied Biosystems) in 10 mM CAPS, 10% (v/v) methanol, pH 11. The blot was stained for 1 minute in 0.1% Coomassie Blue R-250 and destained in 50% (v/v) methanol. The band correspnding to the 75 kD protein was cut out and N-terminal sequence analysis was performed using an Applied Biosystems 470A gas phase protein sequencer equiped with a 120A on-line phenylthiohydantoin analyser. The sequence of 30 amino acids from the N-terminus was obtained and is given as SEQ ID NO 1.

EXAMPLE 4

Method to identify, isolate and characterise a cDNA clone encoding tomato fruit β-1,4 galactanase The N-terminal amino acid sequence (SEQ ID NO 1) is used to design degenerate oligo-nucleotide probes for screening tomato fruit cDNA libraries. The following probes may be used: KAH3 (SEQ ID NO 3), KAH10 (SEQ ID NO 4) and KAH11 (SEQ ID NO 5). In SEQ ID NO 3, SEQ ID NO 4 and SEQ ID NO 5 the symbol "N" represents an inosine base.

250,000 clones from a cDNA library made from RNA breaker stage fruit (cv. VFN8) in lambda gt11 (Clontech) are plated, transferred to nylon membranes and screened with $^{32}$P labelled oligo KAH3. Hybridisation is performed in 5xSSC, 0.25% Dried skimmed milk, 0.01% SDS at 30° C. for 16hr. The membranes are washed in 6xSSC, 0.1% SDS at 30° C. prior to autoradiography. Hybridising plaques are purified and DNA is prepared for characterisation.

Using appropriate hybridisation and washing conditions, other degenerate oligonucleotide probes (designed from β-galactonase amino acid sequence) are used to screen tomato cDNA libraries in order to identify clones encoding β-galactanase.

Clones hybridising to β-galactanase oligonucleotide probes are characterised by sequence analysis in order to identify open reading frame that encode the enzyme.

EXAMPLE 5

Identification, isolation and characterisation of the cDNA clone KH15 encoding galactanase The N-terminal amino acid sequence of the tomato galactanase (SEQ ID NO 1) is partially homologous to the N-terminal amino acid sequence of the protein encoded by a senescence related cDNA clone (pSR12) from carnation (Raghothama et al, 1991, Plant Molecular Biology, 17:61–71). The N-terminal segment of the pSR12-encoded protein sequence is shown as SEQ ID NO 6.

The pSR12 clone was used to screen approximately 400,000 clones from a cDNA library made from mRNA from ripening fruit (cv. Ailsa Craig) in lambda gt11 (Clonetech). Hybridisation of the 32 P labelled probe was performed in 5xSSPE, 0.25% dried milk powder, 0.01% SDS at 55° C. for 16 hr. The membranes were washed in 6xSSC, 0.1% SDS at 55° C. prior to autoradiography. A hybridising plaque was identified and purifed to homogeneity (labelled clone KH15).

Clone KH15 contained an EcoRI insert of about 3 Kb. This was sub-cloned into pUC19 and the nucleotide sequence was determined (SEQ ID NO 2). The sequence encoded an open-reading frame (bases 75 to 2582) for a 836 amino acid protein. The N-terminal segment of the predicted protein sequence encoded by clone KH15 is shown as SEQ ID NO 7. SEQ ID NO 7 shows significant homology to the determined tomato galactanase N-terminal sequence (SEQ ID NO 1). These results indicate that clone KH15 encodes a protein very closely related to the purified tomato galactanase.

EXAMPLE 6

Construction of antisense RNA vectors with the CaMV 35S promoter

A vector is constructed using the sequences corresponding to a fragment of the insert of a galactanase cDNA (isolated as shown in example 5). This fragment is synthesised by polymerase chain reaction using synthetic primers. The ends of the fragment are made flush with T4 polymerase and it is cloned into the vector pJR1 which has previously been cut with SmaI. pJR1 (Smith et al, 1988, Nature, 334:724–726) is a Bin19 (Bevan, 1984, Nucleic Acids Research, 12:8711–8721) based vector, which permits the expression of the antisense RNA under the control of the CaMV 35S promoter. This vector includes a nopaline synthase (nos) 3' end termination sequence.

A second vector is constructed using a fragment of the galactanase sequence cloned into the vectors GA643 (An et al, 1988, Plant Molecular Biology Manual A3: 1–19) or pDH51 (Pietrzak et al, 1986, Nucleic Acids Research, 14:5875–5869) which has previously been cut with a compatible restriction enzyme(s). A restriction fragment from the galactanase/pDH51 clone containing the promoter, the galactanase clone fragment and other pDH51 sequence is cloned into SLJ44026B or SLJ44024B (Jones et al, 1990, Transgenic Research, 1) or a Bin19 (Bevan, 1984, Nucleic Acids Research, 12:8711–8721) which permits the expression of the antisense RNA under control of the CaMV 35S promoter. After synthesis of the vector, the structure and orientation of the sequences are confirmed by DNA sequence analysis.

EXAMPLE 7

Construction of antisense RNA vectors with a fruit enhanced promoter

The fragment of the galactanase cDNA that was described in Example 6 is also cloned into the vector pJR3. pJR3 is a Bin19 based vector, which permits the expression of the antisense RNA under the control of the tomato polygalacturonase (PG) promoter. This vector includes approximately 5 kb of promoter sequence and 1.8 kb of 3' sequence from the PG promoter separated by a multiple cloning site.

After synthesis, vectors with the correct orientation of the galactanase sequences are identified by DNA sequence analysis.

Alternative fruit enhanced promoters (such as E8 or 2A11) are substituted for the polygalacturonase promoter in pJR3 to give alternative patterns of expression.

EXAMPLE 8

Construction of truncated sense RNA vectors with the CaMV 35S promoter

The fragment of the galactanase cDNA that was described in Example 6 is also cloned into the vectors described in Example 6 in the sense orientation.

After synthesis, the vectors with the sense orientation of the galactanase sequence are identified by DNA sequence analysis.

For example, a 376 bp PCR fragment (from base 1 to 376) from clone KH15 was cloned into pBluescript (Strategene), excised as a SmaI-SalI and cloned into pUC19. The fragment was excised as a KpnI-SalI fragment and cloned directly into pJR1Ri. The correct construction of the vector was confirmed by DNA sequence analysis and it was labelled pBIN-KH15.

EXAMPLE 9

Construction of truncated sense RNA vectors with fruit-enhanced promoter

The fragment of the galactanase cDNA that was described in Example 6 is also cloned into the vector pJR3 in the sense orientation.

After synthesis, the vectors with the sense orientation of the galactanase sequence are identified by DNA sequence analysis.

Alternative fruit enhanced promoters (eg E8 or 2A11) are substituted for the polygalacturonase promoter in pJR3 to give alternative patterns of expression.

EXAMPLE 10

Construction of a galactanase over-expression vector using the CaMV35S promoter

The complete sequence of a galactanase cDNA containing a full open-reading frame is inserted into the vectors described in Example 6.

EXAMPLE 11

Construction of a galactanase over-expression vector using a fruit-enhanced promoter The complete sequence of a galactanase cDNA containing a full open-reading frame is inserted into pJR3 or alternatives with different promoters.

EXAMPLE 12

Generation of transformed plants

Vectors are transferred to *Agrobacterium tumefaciens* LBA4404 (a micro-organism widely available to plant biotechnologists) and are used to transform tomato plants. Transformation of tomato stem segments follow standard protocols (e.g. Bird et al, 1988, Plant Molecular Biology, 11:651–662). Transformed plants are identified by their ability to grow on media containing the antibiotic kanamycin. Plants are regenerated and grown to maturity. Ripening fruit are analysed for modifications to their ripening characteristics.

Transformation experiments to incorporate PBIN-KH15 into tomato (cv. Ailsa Craig) have produced 27 transgenic plants. These plants are being grown for analysis.

We claim:

1. A DNA construct comprising a DNA sequence encoding a galactanase protein which is encoded by SEQ ID NO 2.

2. A DNA construct as claimed in claim 1 in which the DNA sequence is contained in the clone deposited at The National Collections of Industrial and Marine Bacteria on 11 May 1994 under the accession number NCIMB 40639.

3. A DNA construct as claimed in claim 1 in which the DNA sequence is as shown in SEQ ID NO 2.

4. A plant cell transformed with a DNA construct as claimed in claim 1.

5. A plant derived from a plant cell as claimed in claim 4.

6. A plant cell transformed with a DNA construct as claimed in claim 3.

7. A plant derived from a plant cell as claimed in claim 6.

8. A plant cell transformed with a DNA construct as claimed in claim 2.

9. A plant derived from a plant cell as claimed in claim 8.

\* \* \* \* \*